(12) United States Patent
Du Plessis

(10) Patent No.: US 7,104,969 B2
(45) Date of Patent: Sep. 12, 2006

(54) SAFETY SYRINGE

(75) Inventor: Johannes Stephanus Du Plessis, Lichtenburg (ZA)

(73) Assignee: Ventradex AG, Attelwil (CH)

( * ) Notice: Subject to any disclaimer, the term of this patent is extended or adjusted under 35 U.S.C. 154(b) by 753 days.

(21) Appl. No.: 09/906,112

(22) Filed: Jul. 17, 2001

(65) Prior Publication Data
US 2002/0010422 A1   Jan. 24, 2002

(30) Foreign Application Priority Data
Jul. 18, 2000  (ZA) ................................ 2000/3593

(51) Int. Cl.
*A61M 5/00* (2006.01)
*A61M 5/32* (2006.01)

(52) U.S. Cl. ...................... 604/110; 604/198
(58) Field of Classification Search ................ 604/110, 604/187, 192–198, 163, 263, 181; 128/919
See application file for complete search history.

(56) References Cited

U.S. PATENT DOCUMENTS

| 5,226,881 A |   | 7/1993 | Pickhard |
|---|---|---|---|
| 5,342,320 A | * | 8/1994 | Cameron .................... 604/192 |
| 5,368,568 A | * | 11/1994 | Pitts et al. .................. 604/110 |
| 5,788,677 A |   | 8/1998 | Botich et al. |
| 6,074,370 A | * | 6/2000 | Pressly et al. ............... 604/195 |
| 6,123,688 A |   | 9/2000 | Botich et al. |
| 6,565,540 B1 | * | 5/2003 | Perouse et al. ............. 604/192 |

FOREIGN PATENT DOCUMENTS

| AT | 395679 |   | 2/1993 |
|---|---|---|---|
| EP | 0438368 |   | 7/1991 |
| FR | 2741268 | * | 11/1995 |
| FR | 2741168 | * | 5/1997 |
| FR | 2741268 |   | 5/1997 |
| WO | WO 99/59658 | * | 11/1999 |

* cited by examiner

*Primary Examiner*—Nicholas D. Lucchesi
*Assistant Examiner*—Matthew F. DeSanto
(74) *Attorney, Agent, or Firm*—Greenblum & Bernstein, P.L.C.

(57) ABSTRACT

Safety syringe that includes a cylindrical chamber having a front end that includes a discharge end, a plunger slidably coupled to the cylindrical chamber, and a needle holder structured to receive a needle having at least a portion of which that protrudes from the discharge end. A cylinder unit is slidably arranged within the front end, and a plunger seal, coupled to the plunger, is arranged for movement relative to the plunger after medicament discharge. The plunger is arranged to slidably move the cylinder unit toward the discharge end and to slidably dislodge the plunger seal. The cylinder unit is structured to provide a protective shield around the portion of the needle protruding from the discharge end.

2 Claims, 1 Drawing Sheet

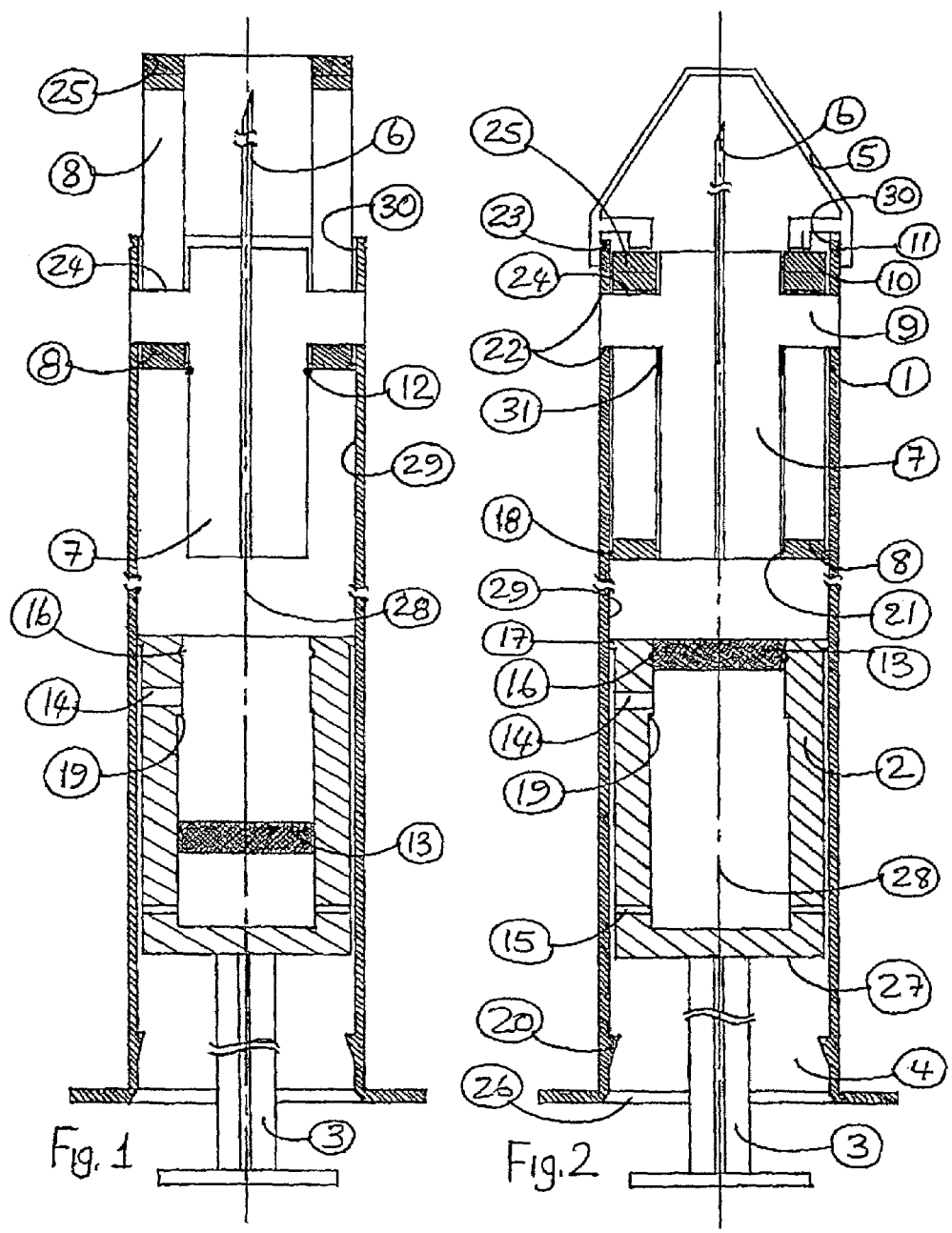

SAFETY SYRINGE

CROSS-REFERENCE TO RELATED APPLICATIONS

The present application claims priority under 35 U.S.C. § 119 of South African Patent Application No. 200 03 593, filed on Jul. 18, 2000, the disclosure of which is expressly incorporated by reference herein in its entirety.

BACKGROUND OF THE INVENTION

1. Field of the Invention

The present invention relates to a syringe having a chamber with tubular cylindrical configuration. A plunger within the tubular cylindrical configuration is able to move along an axial axis of the tubular cylindrical configuration and a needle holder configuration is externally fixed or integrally part to the discharge end of the tubular cylindrical configuration of the syringe, i.e., opposite the plunger handle.

2. Discussion of Background Information

The needle holder configuration connects to the discharge end of the syringe via a one piece receptacle module, which allows the connection to be done either externally or as an integral part of the syringe tubular configuration. In this manner, it is possible to cover and protect the protrusive needle portion after medicament discharge via a protruding shield extending internally from the tubular cylindrical configuration of the syringe chamber front end. Thus, the discharge end, actuated by the force exerted on the rear end of the plunger handle directly after medicament discharge, is moved, in a same axial direction as for medicament discharge, to the most forward position of the plunger to counter any accidental contact with the needle portion during further handling.

Other embodiments of such conventional safety syringes may have a number of shortcoming, e.g., the needle holder configuration or device has to be inserted from the non-discharge end (i.e., rear end) of the syringe; needles of different sizes cannot be accommodated on the syringe; increased production costs and assembling difficulties due to plug type embedments into the discharge end of the syringe; a considerable degree of complexity as if for special applications only; and unofficial re-use possibility of syringe after initial usage, which can cause extremely unsafe conditions, due to a slight reactivation force onto certain components of the syringe so as to reconstruct the syringe as if for initial use.

SUMMARY OF THE INVENTION

According to the present invention, a safety syringe includes a needle holder connected to, or as an integral part of, a tubular cylindrical discharge end of the syringe, and accommodates a receptor and seal to form a discharge end seal. The syringe also includes a plunger, which is slidably contained in the syringe, which is limited to only one use via a plunger seal arranged to prevent further use of the plunger. The plunger includes a cylindrical section communicating, e.g., directly after medicament discharge, with the receptor, thus deactivating the seal of the needle holder and the plunger seal almost simultaneously via further axial movement of the plunger in the direction of the discharge end (i.e., toward the needle portion) to a fixed distance traveled, i.e., against a forwardmost stop for the receptor to such an extent that the receptor is locked in the most forward position through which a shield is permanently provided to cover the entire needle portion.

Thus, the entire syringe mechanism is rendered useless in that the entire needle portion is shielded off against any accidental contact and the plunger is destructively changed so as not to reseal within the tubular cylindrical configuration of the syringe. In this manner, both the discharged end and the rear end of the syringe are left inoperable to neither allow the possibility of suction nor compression during any further operation of the plunger handle. Based on the configuration explained, and during the plunger advancement during the injection phase and when reaching the most forward position to fully discharge the medicament, the cylindrical section of the plunger, with continued pressing the plunger handle towards the discharge end of the syringe, communicates directly with the non-discharge end of the receptor cylindrical section, which preferably has a same outer diameter and seal diameter as the plunger, but is slightly larger in cylindrical internal diameter than the outer diameter of the rear end of the configurative needle holder portion. In accordance with this construction, the plunger allows, without binding movement on the needle holder portion, the receptor to be pushed forward towards the discharge end of the syringe to such a position, as to lock in its most forward position and to provide a shield around the protrusive needle portion, thereby rendering the needle portion protected during further handling of the said syringe. During the stage when the plunger is pushed towards the discharge end of the syringe, i.e., just after complete medicament discharge, and when the cylindrical portion of the plunger is moving against the cylindrical portion of the receptor, thus, axially sliding over the rear end portion of the needle holder and during the deactivation of the receptor seal and needle holder seal, the seal of the hollow cylindrical plunger is likewise deactivated such that no seal exists any longer to form a closed cylindrical chamber to provide a basis of a syringe internal chamber principal into which a volume of liquid may be contained.

From this position the advancement of the plunger handle may proceed to lock the receptor in its most forward position.

At this stage the syringe is rendered useless to any further use and may thus be discarded.

The present invention is directed to a safety syringe that includes a cylindrical chamber having a front end that includes a discharge end, a plunger slidably coupled to the cylindrical chamber, and a needle holder structured to receive a needle having at least a portion of which that protrudes from the discharge end. A cylinder unit is slidably arranged within the front end, and a plunger seal, coupled to the plunger, is arranged for movement relative to the plunger after medicament discharge. The plunger is arranged to slidably move the cylinder unit toward the discharge end and to slidably dislodge the plunger seal. The cylinder unit is structured to provide a protective shield around the portion of the needle protruding from the discharge end.

According to a feature of the instant invention, the plunger can include a cylindrical space having an opening positioned at an end arranged to face the discharge end, and the plunger seal can be positioned in the opening. The needle holder may include a surface arranged to move the plunger seal, after complete medicament discharge, relative to the plunger. Further, a locking device can be arranged to lock the cylinder unit in a position at which the protective shield is provided. The plunger can substantially simultaneously slide the cylinder unit into the protective shield position and dislodge the plunger seal. Still further, when the plunger seal is dislodged, at least a portion of the cylindrical space can be structured to receive the plunger seal in a non-sliding manner. Moreover, when the plunger seal is dislodged, the safety syringe may be rendered useless.

In accordance with another feature of the instant invention, the cylindrical unit can include a rear seal formed on an end remote from the discharge end. The rear seal may include an inner seal portion arranged to abut the needle holder and an outer seal portion arranged to abut the cylindrical chamber.

The plunger may include at least one seal arranged on an outer diameter of the plunger to abut the cylindrical chamber.

Further, the syringe may be adaptable to different lengths of needles. Still further, the syringe can be adaptable to different lengths of needle holders.

Moreover, a space can be formed within the plunger comprising a first and a second cylindrical space, in which the first and second cylindrical spaces have different diameters and are coupled to each other to form a step change. The plunger can include an aperture positioned before the step change, in a plunger seal movement direction, and the aperture can be formed in the cylinder space having the smaller diameter. Further still, the plunger can further include air holes arranged toward an end of plunger remote from the discharge end, which are located to pass air within the space as the plunger seal is moved.

In accordance with still another feature of the present invention, an end cap may be removably coupled over the discharge end prior to use. The end cap can include a stop device arranged to restrict movement of the cylinder unit while the end cap is coupled over the discharge end. Further, the safety cap may include screw threads to removably couple the safety cap over the discharge end.

The present invention is directed to a safety syringe that includes a cylindrical chamber having a front end that includes a discharge end, a plunger slidably coupled to the cylindrical chamber, and a needle holder structured to receive a needle. A cylinder unit is slidably arranged within the front end, and a plunger seal, coupled to the plunger, is arranged for movement relative to the plunger after medicament discharge. The plunger is arranged to slidably move the cylinder unit toward the discharge end and to slidably dislodge the plunger seal to prevent reuse of the safety syringe. The cylinder unit is structured to provide a protective shield around the portion of needle protruding from the discharge end.

According to a feature of the invention, the needle holder can include, a surface arranged to move the plunger seal relative to the plunger.

A cylinder unit seal can be positioned between the needle holder and the cylindrical chamber, and a locking device may be arranged to lock the cylinder unit seal to prevent reuse of the safety syringe.

In accordance with yet another feature of the present invention, the plunger can substantially simultaneously slide the cylinder unit into the protective shield position and dislodge the plunger seal.

Other exemplary embodiments and advantages of the present invention may be ascertained by reviewing the present disclosure and the accompanying drawings.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 1 is a sectional view showing all parts in construction of a syringe in accordance with the invention with the plunger in its rearranged layout after medicament discharge and with the needle protector in its most forward position; and FIG. 2 is a sectional view showing all parts in construction of a syringe in accordance with the invention and in a pre-use layout.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

As shown in FIGS. 1 and 2, the present invention is directed to a safety syringe that includes a cylindrical chamber 1 arranged to receive a plunger 2, which is capable of axially moving in a hollow cylindrical portion 29. Cylindrical portion 29 is open on its rear end 4, and its front end is formed at an open cylindrical end 30, into which a cylindrical slidable unit 8 is at least partially contained around a needle holder 7, which forms a closure to syringe front end 30. Needle holder 7 and cylindrical slidable unit 8 are interconnected to each other and coupled to cylindrical chamber 1. In particular, needle holder 7 is arranged to be slidable within cylindrical slidable unit 8, and the combination of needle holder 7 and cylindrical slidable unit 8 are arranged within the cylindrical chamber 1 via the insertion of at least one male protrusion 9 into at least one female receptacle area 22, e.g., near or at the front end (i.e., discharge end) of the syringe. Moreover, needle 6 can be protected, e.g., prior to use, by a protective cap 5, which remains in place until a time of use, at which time, protective cap 5 may be removed, e.g., via a radial twisting action on protective cap 5, thereby detachably releasing cap 5 from cylindrical chamber 1.

Hollow cylindrical portion 29 is adapted to be filled with liquid medicament via a sliding action of plunger 2 towards rear end 4 of cylindrical chamber 1. Plunger 2 includes a plunger handle 3 on its rear end and a hollow cylindrical plunger head having a seal 13 arranged to close off the syringe discharge end. Plunger 2 can be specifically configured to include radial groove 16, which is provided to contain and restrict movement of seal means 13 in order to increase initial slidable friction. After complete medicament discharge, seal 13 can be pushed toward rear end 4 by pushing plunger handle 3 toward the syringe discharge end. In this manner, the rear end of needle holder 7 restricts the movement of seal 13, as plunger handle 3 continues to move toward the syringe discharge end, i.e., both seal 13 and plunger handle 3 moved relative to each other along cylindrical axes 28. As plunger handle 3 continues to move relative to seal 13, aperture 14 moves to and beyond seal 13, which opens plunger 2. In this way, the sealing effect of plunger 2 is disabled, which renders the plunger 2 incapable for further sealing, suction or compression.

When seal 13 is pushed toward rear end 4, air escape routes 15 allow normal atmospheric pressure inside the rear end portion of plunger 7 and the rear end face of seal 13. Moreover, plunger 2 is rendered useless for further use, since, as it is formed to have slightly larger outer diameter than the internal diameter starting at diametrical step change 19, seal 13 cannot move toward the discharge end of the syringe by any natural slidable movement.

During actual movement of plunger 2 toward the discharge end of the syringe, plunger 2 slidably moves over the rear end portion of needle holder 7, which has a lesser outer diameter than the internal diameter of plunger 2, thus, causing the cylindrical slidable unit 8 to be pushed forward in the direction of the syringe discharge, i.e., to a forwardmost position where cylindrical slidable unit 8 is positively locked onto needle holder 7 at a front end portion via lock 12. At this stage, cylindrical slidable unit 8 extends or protrudes to a forwardmost position to a fixed distance sufficient to cover and protect needle 6, i.e., in excess of distance by which needle 6 protrudes from the syringe.

In this position, seal 21 of cylindrical slidable unit 8 engaged with needle holder 7 and seal 18 of cylindrical slidable unit 8 engaged with hollow cylindrical portion 29 are likewise rendered useless due to a slight cylindrical step change 31 on needle holder 7 at positive lock 12.

Thus, the entire syringe is rendered useless due to the destruction of the sealing interface between seal 13 and the internal diameter of plunger 2 and the inadequate seal between cylindrical chamber 1, cylindrical slidable unit 8 and needle holder 7. Plunger 2 is stopped positively on the rearwardmost cylindrical face 27 against stop 20, which can be integrally formed in the construction of cylindrical chamber 1. Taper edge 26 is provided to allow easy access into cylindrical chamber 1 for plunger 2. A seal 17 is provided on the outer diameters of plunger 2 to allow for a seal between plunger means 2 and hollow cylindrical portion 29. Cylindrical slidable unit 8 front end 25 has a positive stop 24 on at least one male protrusion 9 in its most rearward configurative position prior to use.

According to the invention, accidental activation of the syringe prior to use is countered by front cylindrical stop section 25 of cylindrical slidable unit 8 being stopped against at least one stop 10, which can be integrally formed as part of needle protective cap 5. Moreover, front cylindrical stop section 25 can be held in position prior to use by at least one male protrusion 11 in protective cap 5 (or in cylindrical chamber 1) arranged to engage at least one female aperture 23 formed in cylindrical chamber 1 (or in protective cap 5), thereby preventing movement of cylindrical slidable unit 8 prior to use of the syringe. This arrangement can be utilized to form, e.g., a screw connection.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A safety syringe comprising:
    a cylindrical chamber having a front end that includes a discharge end;
    a plunger slidably coupled to said cylindrical chamber;
    a needle holder structured to receive a needle having at least a portion of which that protrudes from said discharge end;
    a cylinder unit slidably arranged within said front end;
    a plunger seal coupled to said plunger which is arranged for movement relative to said plunger after medicament discharge; and
    said plunger being arranged to slidably move said cylinder unit toward said discharge end and to slidably dislodge said plunger seal,
    wherein said cylinder unit is structured to provide a protective shield around the portion of the needle protruding from said discharge end,
    wherein a space is formed within said plunger comprising a first and a second cylindrical space, said first and second cylindrical spaces having different diameters and being coupled to each other to form a step change, and
    wherein said plunger comprises an aperture positioned before said step change, in a plunger seal movement direction, said aperture being formed in the cylinder space having the smaller diameter.

2. The safety syringe in accordance with claim 1, wherein said plunger further comprises air holes arranged toward an end of plunger remote from said discharge end, said air holes being located to pass air within said space as said plunger seal is moved.

* * * * *

UNITED STATES PATENT AND TRADEMARK OFFICE
CERTIFICATE OF CORRECTION

PATENT NO. : 7,104,969 B2 Page 1 of 1
APPLICATION NO. : 09/906112
DATED : September 12, 2006
INVENTOR(S) : J. Du Plessis It is certified that error appears in the above-identified patent and that said Letters Patent is hereby corrected as shown below:

On the cover page, Item (56) Foreign Patent Documents, remove "FR 2741268 11/1995" in its entirety.

On the cover page, Item (56) Foreign Patent Documents, remove "FR 2741168 5/1997" in its entirety.

Signed and Sealed this

Third Day of June, 2008

JON W. DUDAS
*Director of the United States Patent and Trademark Office*